US012797595B2

(12) United States Patent
Rampa et al.

(10) Patent No.: US 12,797,595 B2
(45) Date of Patent: Nov. 17, 2026

(54) HEMOSTASIS VALVE FOR EXPANDABLE-TYPE CATHETER

(71) Applicant: Biosense Webster (Israel) Ltd., Yokneam (IL)

(72) Inventors: Sreekanth Reddy Rampa, Irvine, CA (US); Robert Kato, Irvine, CA (US); Roozbeh Borjian, Irvine, CA (US); Michael Banando, Glendora, CA (US); Jose Jimenez, Ontario, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 374 days.

(21) Appl. No.: 18/597,609

(22) Filed: Mar. 6, 2024

(65) Prior Publication Data

US 2024/0335648 A1 Oct. 10, 2024

Related U.S. Application Data

(60) Provisional application No. 63/494,930, filed on Apr. 7, 2023.

(51) Int. Cl.
*A61M 39/06* (2006.01)
*A61B 17/00* (2006.01)

(52) U.S. Cl.
CPC ......... *A61M 39/0606* (2013.01); *A61B 17/00* (2013.01); *A61B 2017/0046* (2013.01); *A61M 2039/062* (2013.01); *A61M 2039/064* (2013.01)

(58) Field of Classification Search
CPC ........ A61M 39/0606; A61M 2039/062; A61M 2039/064; A61M 2039/0653; A61M 2039/0685; A61B 2017/12004
See application file for complete search history.

(56) References Cited

U.S. PATENT DOCUMENTS

| | | | | |
|---|---|---|---|---|
| 5,102,395 A * | 4/1992 | Cheer | A61M 39/0606 604/167.03 |
| 5,391,199 A | 2/1995 | Ben-Haim | |
| 5,443,489 A | 8/1995 | Ben-Haim | |
| 5,536,261 A * | 7/1996 | Stevens | A61M 25/007 604/523 |

(Continued)

FOREIGN PATENT DOCUMENTS

EP 1101447 B1 4/2005

OTHER PUBLICATIONS

Extended European Search Report and Opinion dated Aug. 30, 2024, from corresponding European Application No. 24168739.1.

*Primary Examiner* — Laura A Bouchelle

(57) ABSTRACT

The disclosed technology includes a hemostasis valve assembly comprising an elongate body with a first valve disposed near the proximal end and a second valve disposed near the distal end and spaced apart from the first valve. The first valve can allow a member to extend through the first valve and the second valve can allow the member to extend through the second valve. The elongate body can define a cavity comprising a sloped portion including a first distance between an inner surface of the elongate body and the longitudinal axis near the distal end that is greater than a distance between the inner surface and the longitudinal axis near the proximal end such that a gas is directed along the sloped portion to accumulate at an accumulation region in the cavity near the distal end when a member extends through the first valve.

18 Claims, 12 Drawing Sheets

(56) References Cited

U.S. PATENT DOCUMENTS

| | | | | |
|---|---|---|---|---|
| 5,558,091 | A | 9/1996 | Acker et al. | |
| 6,172,499 | B1 | 1/2001 | Ashe | |
| 6,190,357 | B1 * | 2/2001 | Ferrari | A61M 25/0023 604/523 |
| 6,239,724 | B1 | 5/2001 | Doron et al. | |
| 6,332,089 | B1 | 12/2001 | Acker et al. | |
| 6,484,118 | B1 | 11/2002 | Govari | |
| 6,618,612 | B1 | 9/2003 | Acker et al. | |
| 6,690,963 | B2 | 2/2004 | Ben-Haim et al. | |
| 6,788,967 | B2 | 9/2004 | Ben-Haim et al. | |
| 6,892,091 | B1 | 5/2005 | Ben-Haim et al. | |
| 7,536,218 | B2 | 5/2009 | Govari et al. | |
| 7,756,576 | B2 | 7/2010 | Levin | |
| 7,848,787 | B2 | 12/2010 | Osadchy | |
| 7,869,865 | B2 | 1/2011 | Govari et al. | |
| 8,456,182 | B2 | 6/2013 | Bar-Tal et al. | |
| 9,974,938 | B2 * | 5/2018 | Pepin | A61M 25/0668 |
| 2005/0027253 | A1 * | 2/2005 | Castellano | A61M 1/3627 604/122 |
| 2006/0264834 | A1 | 11/2006 | Vaillancourt | |
| 2013/0053693 | A1 | 2/2013 | Breznock et al. | |
| 2018/0001037 | A1 | 1/2018 | Shivkumar et al. | |

* cited by examiner

HEMOSTASIS VALVE FOR EXPANDABLE-TYPE CATHETER

CROSS REFERENCE TO RELATED APPLICATIONS

This application claims the benefit of priority under 35 U.S.C. § 119 to prior filed U.S. Provisional Patent Application No. 63/494,930, filed Apr. 7, 2023, the entire contents of which is hereby incorporated by reference as if set forth in full herein.

FIELD

The present invention relates generally to hemostasis valves configured to prevent air from entering a patient's vasculature.

BACKGROUND

A "delivery sheath," "sheath," or "sheath introducer" includes a tube placed in an artery or vein of a patient during a medical procedure that, when positioned for treatment, has a distal end within the artery or vein and a proximal end outside of the patient. A hemostasis valve at the proximal end of the delivery sheath inhibits blood from exiting the sheath and allows longer sheaths and/or catheters to be inserted through the delivery sheath into the artery or vein.

A problem with some current delivery sheaths for catheter delivery is that air can be introduced into the delivery sheath when inserting catheters with somewhat complex geometries (e.g., basket catheter, balloon catheters) through the hemostasis valve. This is because the geometry of some catheters can entrap small air bubbles when in a collapsed form, thereby introducing the air bubbles through the hemostasis valve. As is known, introducing air into the patient's vasculature can cause adverse health effects and should be avoided. The technology disclosed herein addresses these issues.

SUMMARY

There is provided, in accordance with an example of the present invention, a hemostasis valve assembly comprising an elongate body extending along a longitudinal axis and comprising a proximal end, a distal end, and a lumen extending therethrough. The hemostasis valve assembly further comprises a first valve disposed near the proximal end of the elongate body. The first valve can be configured to allow a member to extend through the first valve. The hemostasis valve assembly further comprises a second valve disposed near the distal end of the elongate body spaced apart from the first valve. The second valve can be configured to allow the member to extend through the second valve.

The elongate body of the hemostasis valve assembly can define a cavity comprising a sloped portion. The sloped portion can include a first distance between an inner surface of the elongate body and the longitudinal axis near the distal end that is greater than a distance between the inner surface of the elongate body and the longitudinal axis near the proximal end such that a gas is directed along the sloped portion to accumulate at an accumulation region in the cavity near the distal end when a member extends through the first valve.

There is provided, in accordance with an example of the present invention, a handle for a catheter device. The handle can comprise a housing extending along a longitudinal axis. The housing can be configured for attachment to an insertion tube and comprising an inner chamber.

The handle can comprise a hemostasis valve assembly disposed at least partially in the inner chamber. The hemostasis valve assembly can comprise an elongate body extending along the longitudinal axis and comprising a proximal end, a distal end, and a lumen extending therethrough. The hemostasis valve assembly can comprise a first valve disposed near the proximal end of the elongate body and a second valve disposed near the distal end of the elongate body.

The elongate body can define a cavity comprising a sloped portion. The sloped portion can include a first distance between an inner surface of the elongate body and the longitudinal axis near the distal end that is greater than a distance between the inner surface of the elongate body and the longitudinal axis near the proximal end such that a gas is directed along the sloped portion to accumulate at an accumulation region in the cavity near the distal end.

Additional features, functionalities, and applications of the disclosed technology are discussed in more detail herein.

BRIEF DESCRIPTION OF THE DRAWINGS

FIG. 8A is a front perspective view of the hemostasis valve while

DETAILED DESCRIPTION

Figure 1:
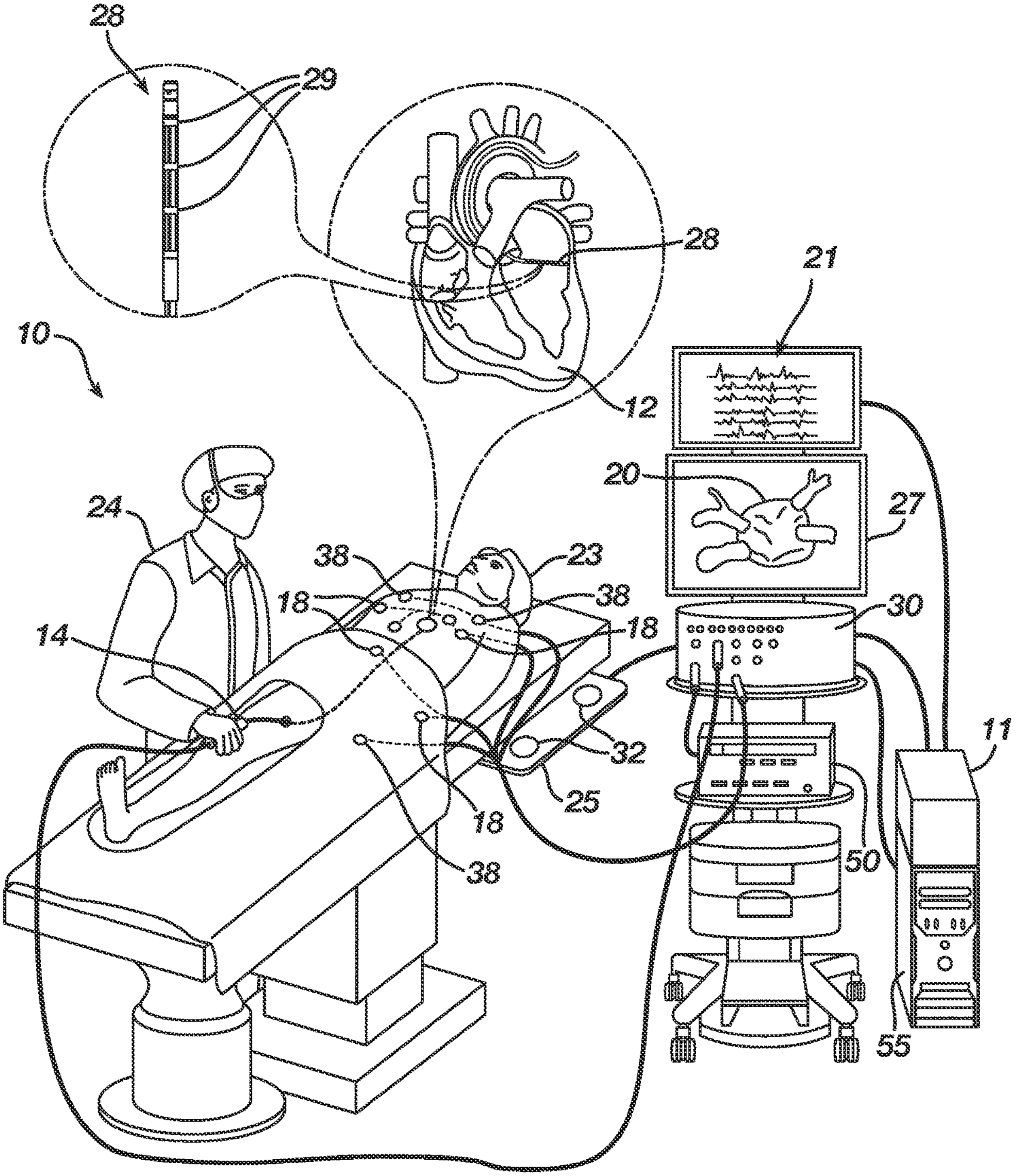
FIG. 1 is a schematic pictorial illustration of a medical system including a delivery sheath and handle, in accordance with an example of the disclosed technology.

The disclosed technology includes a hemostasis valve assembly that is designed to prevent air from being introduced into a patient's vasculature. The hemostasis valve assembly includes a first valve, a second valve, and a chamber disposed between the first valve and the second valve. As a catheter is introduced through the first valve of the hemostasis valve assembly, air that passes through the first valve can be collected in the chamber and directed away from the second valve by a sloped portion of the body of the hemostasis valve, thereby preventing air from entering a patient's vasculature. The hemostasis valve can be incorporated into a handle of a delivery sheath such that catheters inserted through the hemostasis valve and into the sheath of the delivery sheath are prevented from introducing air into a patient's vasculature. Furthermore, the hemostasis valve assembly can be designed such that the handle can be in several different orientations but air can still be collected in an accumulation region of the chamber. These and other benefits of the disclosed technology and described in further detail herein.

The terms "hemostatic" and "hemostasis" are intended to have the same meaning and can be used interchangeably. Similarly, reference to a "hemostatic valve" and a "hemostasis valve" can be used interchangeably herein and are intended to have the same meaning.

The following detailed description should be read with reference to the drawings, in which like elements in different drawings are identically numbered. The drawings, which are not necessarily to scale, depict selected examples and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 110%. In addition, as used herein, the terms "patient," "host," "user," and "subject" refer to any human or animal subject and are not intended to limit the systems or methods to human use, although use of the subject invention in a human patient represents a preferred embodiment. As well, the term "proximal" indicates a location closer to the operator or physician whereas "distal" indicates a location further away to the operator or physician.

As discussed herein, vasculature of a "patient," "host," "user," and "subject" can be vasculature of a human or any animal. It should be appreciated that an animal can be a variety of any applicable type, including, but not limited thereto, mammal, veterinarian animal, livestock animal or pet type animal, etc. As an example, the animal can be a laboratory animal specifically selected to have certain characteristics similar to a human (e.g., rat, dog, pig, monkey, or the like). It should be appreciated that the subject can be any applicable human patient, for example.

As discussed herein, "physician" can include a doctor, surgeon, technician, scientist, operator, or any other individual or delivery instrumentation associated with delivery of a multi-electrode catheter for the treatment of drug refractory atrial fibrillation to a subject.

As discussed herein, the term "ablate" or "ablation", as it relates to the devices and corresponding systems of this disclosure, refers to components and structural features configured to reduce or prevent the generation of erratic cardiac signals in the cells by utilizing non-thermal energy, such as reversable or irreversible electroporation (IRE), referred throughout this disclosure interchangeably as pulsed electric field (PEF) and pulsed field ablation (PFA), or thermal energy such as radiofrequency (RF) ablation or cryoablation. Ablating or ablation as it relates to the devices and corresponding systems of this disclosure is used throughout this disclosure in reference to thermal or non-thermal ablation of cardiac tissue for certain conditions including, but not limited to, arrhythmias, atrial flutter ablation, pulmonary vein isolation, supraventricular tachycardia ablation, and ventricular tachycardia ablation. The term "ablate" or "ablation" also includes known methods, devices, and systems to achieve various forms of bodily tissue ablation as understood by a person skilled in the relevant art.

As discussed herein, the terms "tubular" and "tube" are to be construed broadly and are not limited to a structure that is a right cylinder or strictly circumferential in cross-section or of a uniform cross-section throughout its length. For example, the tubular structures are generally illustrated as a substantially right cylindrical structure. However, the tubular structures may have a tapered or curved outer or inner surface without departing from the scope of the present disclosure.

FIG. 1 shows an example system 10 that can include a delivery sheath 14 (referred to interchangeably as "delivery sheath catheter 14"). The delivery sheath 14 can be configured for navigating to a patient's 23 heart 12 and for delivery of electrophysiology mapping and ablation catheters (not shown). System 10 can be configured for multiple catheters, which are percutaneously inserted by physician 24 through the patient's 23 vascular system into a chamber or vascular structure of a heart 12. Typically, a delivery sheath catheter 14 is inserted into the left or right atrium near a desired location in heart 12. Thereafter, a plurality of catheters can be inserted into the delivery sheath catheter 14 so as to arrive at the desired location. The plurality of catheters may include catheters dedicated for sensing Intracardiac Electrogram (IEGM) signals, catheters dedicated for ablating and/or catheters dedicated for both sensing and ablating. An example delivery sheath catheter 14 that is configured for sensing IEGM is illustrated herein. Physician 24 brings a distal tip of a mapping catheter into contact with the heart wall for sensing a target site in heart 12. The end effector of the mapping catheter may include a basket catheter, a planar catheter, a focal catheter, a balloon catheter, etc. For ablation, physician 24 similarly brings a distal end of an ablation catheter to a target site for ablating. Similarly, the end effector of the ablation catheter may include a basket catheter, a planar catheter, a focal catheter, a balloon catheter, etc.

Figure 2:
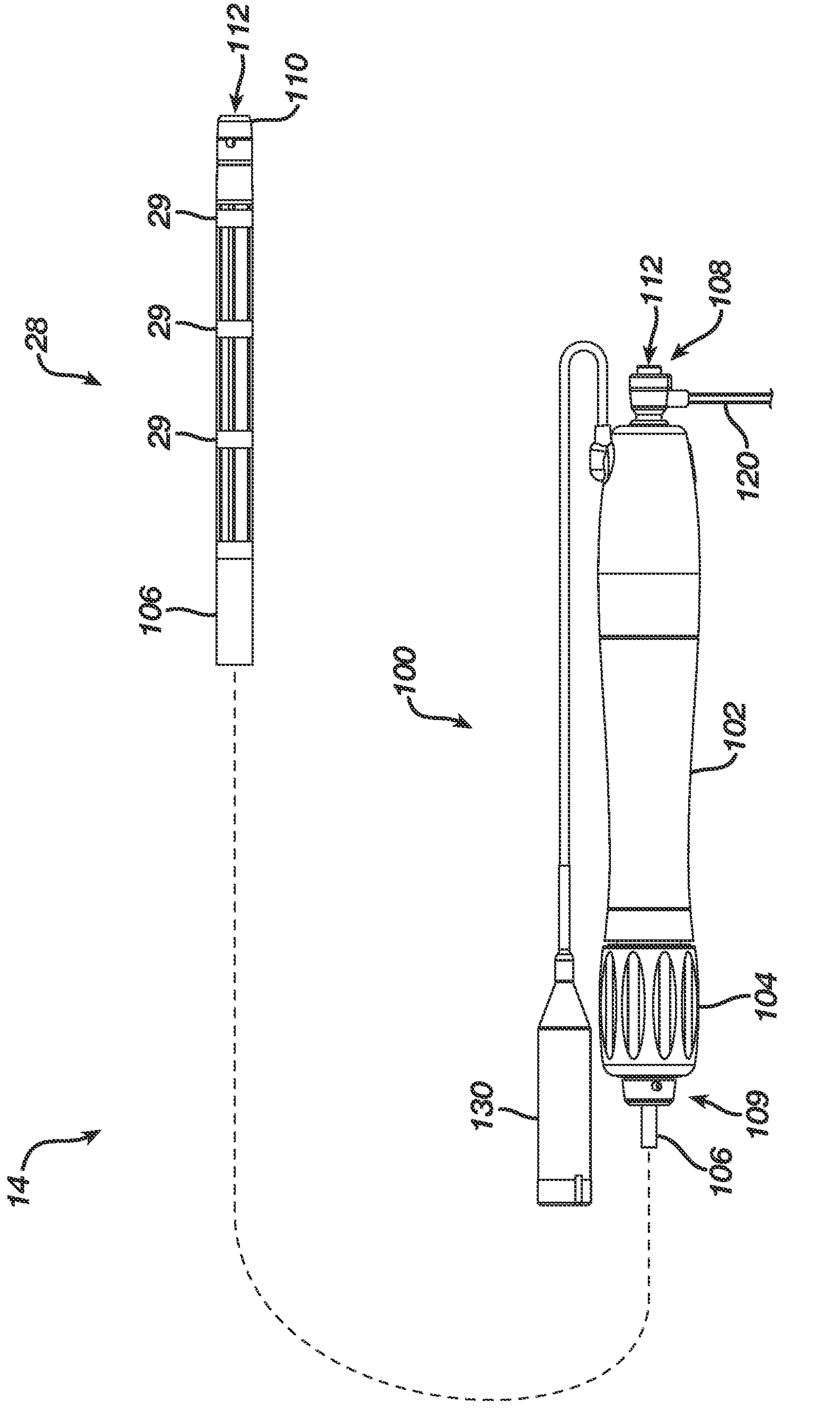
FIG. 2 is a schematic pictorial illustration of a delivery sheath and handle, in accordance with an example of the disclosed technology.

Delivery sheath catheter 14 is an exemplary catheter that includes one and preferably multiple electrodes 29 optionally distributed over a distal end 28 of the delivery sheath catheter 14 for tracking position and orientation of delivery sheath catheter 14. Optionally and preferably, electrodes 29 can be magnetic based position sensors including three magnetic coils for sensing three-dimensional (3D) position and orientation. Alternatively, the position sensor can be configured for impedance-based position tracking. As shown in FIG. 2, delivery sheath catheter 14 can include a handle 100 at a proximal end thereof.

A combination magnetic based position sensor and force sensor may be operated together with a location pad 25 including a plurality of magnetic coils 32 configured to generate magnetic fields in a predefined working volume. Real time position of distal end 28 of delivery sheath catheter 14 may be tracked based on magnetic fields generated with location pad 25 and sensed by magnetic-based position sensors (e.g., electrodes 29). Details of the magnetic based position sensing technology are described in U.S. Pat. Nos. 5,391,199; 5,443,489; 5,558,091; 6,172,499; 6,239,724; 6,332,089; 6,484,118; 6,618,612; 6,690,963; 6,788,967; 6,892,091, each of which are incorporated herein by reference and attached in the Appendix of priority application No. 63/494,930.

System 10 includes one or more electrode patches 38 positioned for skin contact on patient 23 to establish location reference for location pad 25 as well as impedance-based tracking of electrodes 29. For impedance-based tracking, electrical current is directed toward electrodes 29 and sensed at electrode skin patches 38 so that the location of each electrode 29 can be triangulated via the electrode patches 38. Details of the impedance-based location tracking technology are described in U.S. Pat. Nos. 7,536,218; 7,756,576; 7,848,787; 7,869,865; and 8,456,182, each of which are incorporated herein by reference and attached in the Appendix of priority application No. 63/494,930.

A recorder 11 displays electrograms 21 captured with body surface ECG electrodes 18 and intracardiac electrograms (IEGM) captured with electrodes 26 of delivery sheath catheter 14. Recorder 11 may include pacing capability for pacing the heart rhythm and/or may be electrically connected to a standalone pacer.

System 10 may include an ablation energy generator 50 that is adapted to conduct ablative energy to one or more of electrodes at a distal tip of a catheter configured for ablating. Energy produced by ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

Patient interface unit (PIU) 30 is an interface configured to establish electrical communication between catheters, electrophysiological equipment, power supply and a workstation 55 for controlling operation of system 10. Electrophysiological equipment of system 10 may include for example, multiple catheters, location pad 25, body surface ECG electrodes 18, electrode patches 38, ablation energy generator 50, and recorder 11. Optionally and preferably, PIU 30 additionally includes processing capability for implementing real-time computations of location of the catheters and for performing ECG calculations.

Workstation 55 includes memory, processor unit with memory or storage with appropriate operating software loaded therein, and user interface capability. Workstation 55 may provide multiple functions, optionally including (1) modeling the endocardial anatomy in three-dimensions (3D) and rendering the model or anatomical map 20 for display on a display device 27, (2) displaying on display device 27 activation sequences (or other data) compiled from recorded electrograms 21 in representative visual indicia or imagery superimposed on the rendered anatomical map 20, (3) displaying real-time location and orientation of multiple catheters within the heart chamber, and (4) displaying on display device 27 sites of interest such as places where ablation energy has been applied. One commercial product embodying elements of the system 10 is available as the CARTO™ 3 System, available from Biosense Webster, Inc., 31 Technology Drive, Suite 200, Irvine, CA 92618, USA.

FIG. 2 is a schematic pictorial illustration showing a perspective view of a delivery sheath catheter 14 having a handle 100 at a proximal end of the delivery sheath catheter 14 and electrodes 29 disposed on a distal end 28 of the delivery sheath catheter 14. The delivery sheath catheter 14 can be configured for insertion and navigation of a patient's vasculature to position the distal end 28 of the delivery sheath catheter 14 in a chamber of the patient's heart 12.

The delivery sheath catheter 14 can include a handle 100, a coupler 109, and a sheath 106 attached to the handle 100 via the coupler 109 and terminating at a distal end 110 (distal tip). The distal end 110 can include an atraumatic tip configured to prevent injury to tissue. The delivery sheath catheter 14 can include a lumen 112 extending from a proximal end 108 of the handle 100, through the handle 100, and through the sheath 106 all the way to the distal end 110. The lumen 112 can be sized to receive various other catheters including, but not limited to, catheters configured for mapping and/or ablation of tissue.

As mentioned previously, at least the distal end 28 of the sheath 106 can include one or more electrodes 29 configured for position sensing (e.g., magnetic- or impedance-based position tracking). The distal end 28 of the delivery sheath catheter 14 can be configured to deflect in one or more directions to enable steering of the delivery sheath catheter 14. For example, the delivery sheath catheter 14 can include one or more pull wires (not shown) that are attached to an actuator 104 configured to pull the one or more pull wires when actuated to cause the distal end 28 to deflect as will be appreciated by those skilled in the art. The handle 100 can further include a grip 102 configured to be gripped by the physician 24.

The handle 100 can further include an irrigation supply tube 120 that can direct saline or other irrigation fluid from an irrigation supply and into the handle for delivery to the distal end 28. The handle 100 can also include an electrical connector 130 that can be electrically connected to the one or more electrodes 29 and can be configured for connection to the PIU 30.

Figure 3:
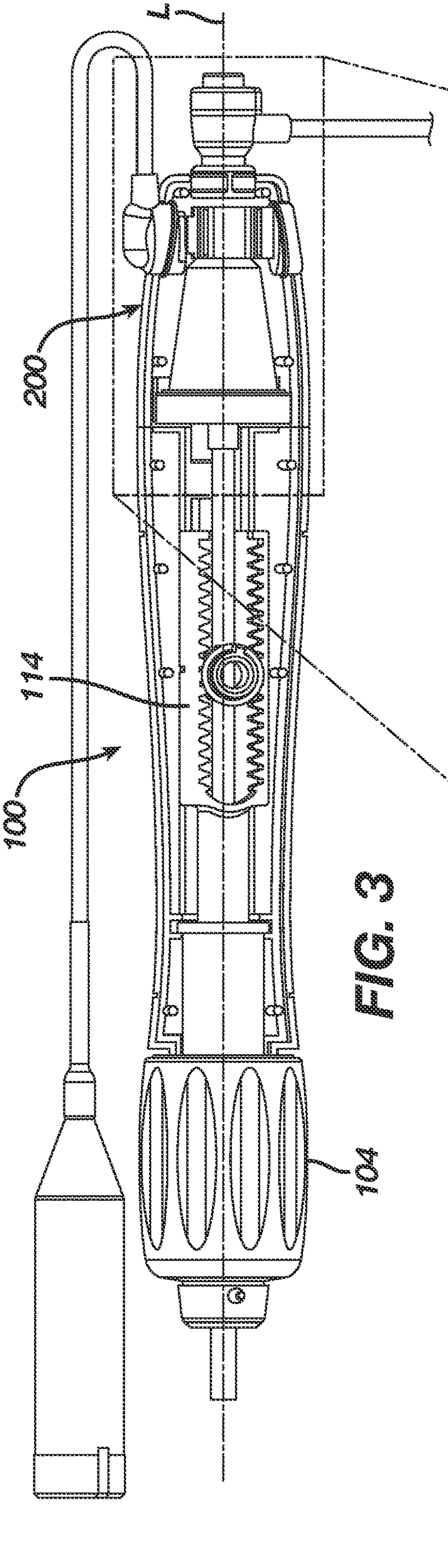
FIG. 3 is a cutaway view of the handle, in accordance with an example of the disclosed technology.
Figure 4:
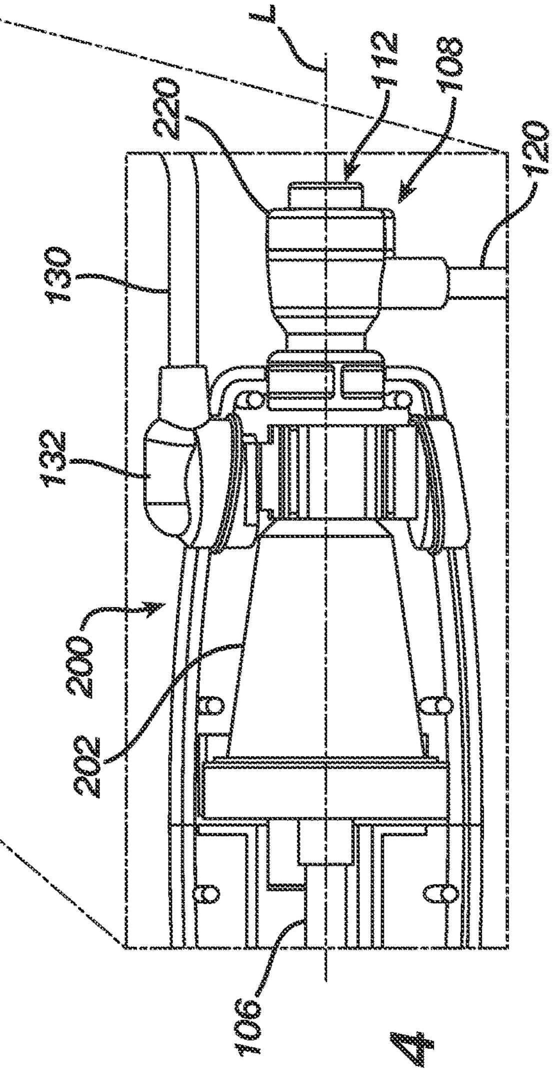
FIG. 4 is a detail view of a hemostasis valve assembly in the handle, in accordance with an example of the disclosed technology.

Turning now to FIGS. 3 and 4, the delivery sheath catheter 14 can include a hemostasis valve assembly 200 that can be configured to prevent air from entering the vasculature of the patient 23. FIG. 3 shows a cutaway view of the handle 100 while FIG. 4 shows a detail view of the hemostasis valve assembly 200.

As shown in FIG. 3, the actuator 104 can be coupled to an actuation assembly 114 that can be attached to one or more pull wires (not shown) and configured to pull the one or more pull wires when actuated to change a direction of the distal end 110. In this way, the distal end 28 of the delivery sheath catheter 14 can be deflected when the actuator 104 is rotated or otherwise actuated by the physician 24. Although the actuator 104 is shown as being a rotary wheel in the drawings, one of skill in the art will appreciate that other actuators can be used instead of a rotary wheel as is known in the art.

Figure 6A:
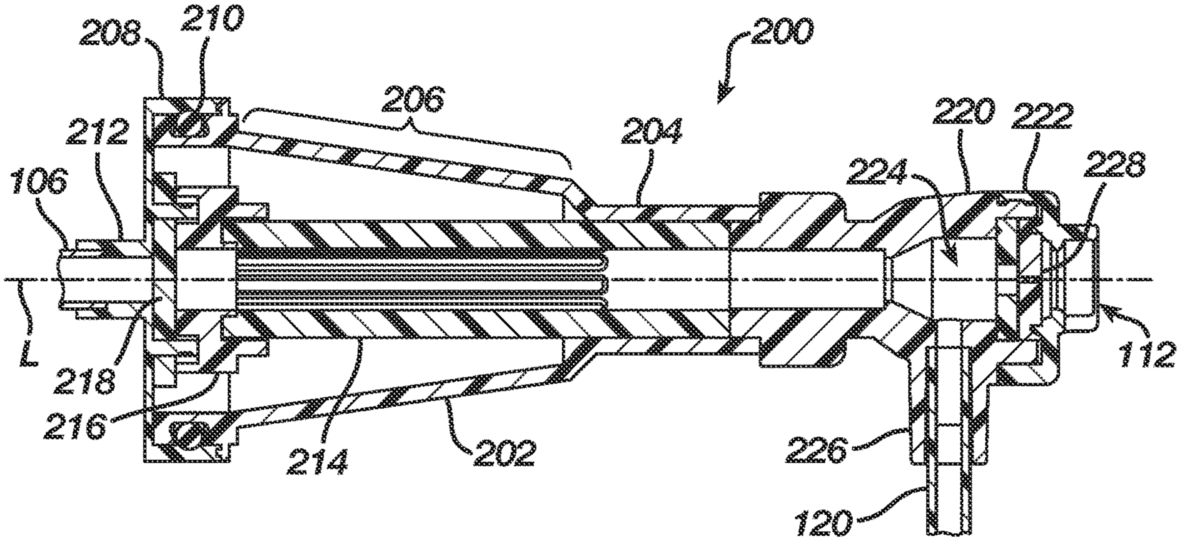
FIG. 6A is a section view showing the components of the hemostasis valve assembly, in accordance with an example of the disclosed technology.

As shown in FIG. 3, the handle 100 can further include a hemostasis valve assembly 200 disposed at least partially in the handle 100. In other words, the handle 100 can form a housing configured to house at least a portion of the hemostasis valve assembly 200. The hemostasis valve assembly 200 can be connected to the irrigation supply tube 120 such that irrigation fluid can enter the hemostasis valve assembly 200 prior to entering the sheath 106 and being delivered into the patient 23. The sheath 106 can be attached directly to the hemostasis valve assembly 200. As shown in FIG. 6A, the irrigation supply tube 120 can be connected to the hemostasis valve assembly 200 downstream of a first valve 228. In this way, the irrigation fluid can enter the hemostasis valve assembly 200 directly while the hemostasis valve assembly 200 prevents blood or other fluids from exiting the hemostasis valve assembly 200.

FIG. 4 also shows the electrical connector 130 including a strain relief 132 attached to the handle 100 and a cord of the electrical connector 130. In this way, the electrical connector 130 can be secured to the handle 100 and prevented from detaching from the handle 100 during an operation.

As shown in FIG. 4, the hemostasis valve assembly 200 can include an expansion chamber body 202 (also referred to as a distal member) and an inlet chamber body 220 (also referred to as a proximal member). In some examples, the expansion chamber body 202 can be positioned inside of the handle 100 while the inlet chamber body 220 can be positioned outside of the handle 100. In other examples, both the expansion chamber body 202 and the inlet chamber body 220 can be positioned outside of the handle 100 or both can be positioned inside of the handle 100. That is, although the hemostasis valve assembly 200 is shown as having the inlet chamber body 220 positioned outside of the handle 100 while the expansion chamber body 202 is positioned inside of the handle, the handle 100 and hemostasis valve assembly 200 can include other configurations without departing from the scope of this disclosure.

Figures 5A, 5B:
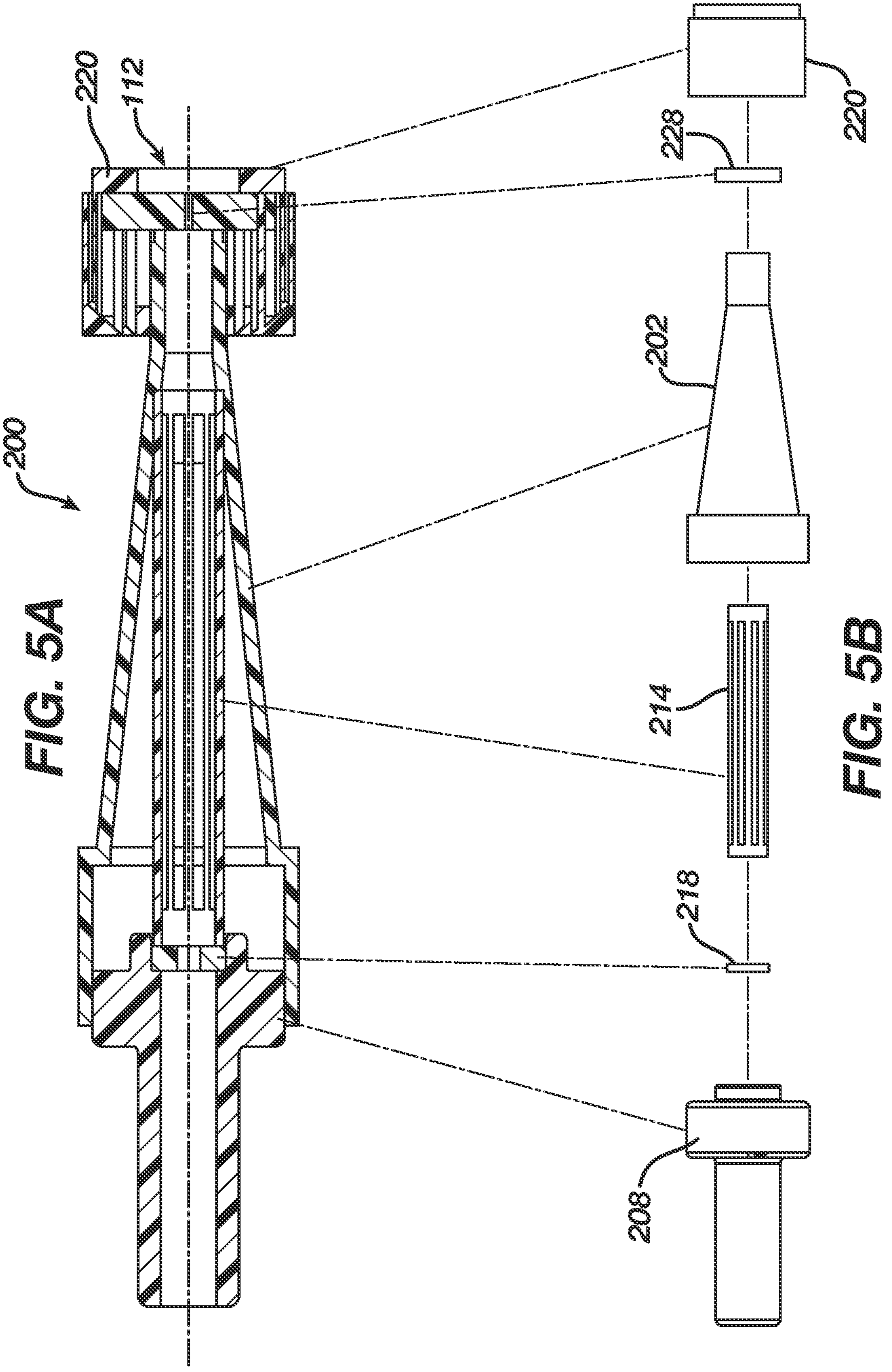
FIG. 5A is a section view and FIG. 5B is an exploded view showing the components of another example of the hemostasis valve assembly, in accordance with an example of the disclosed technology.

FIG. 5A is a section view and FIG. 5B is an exploded view showing the components of the hemostasis valve assembly 200, in accordance with an example of the disclosed technology. As shown in FIGS. 5A and 5B, the hemostasis valve assembly 200 can include a first valve 228 at a proximal end of the hemostasis valve assembly 200 and a second valve 218 at a distal end of the hemostasis valve assembly 200. The first valve 228 and the second valve 218 can each be configured to prevent fluid from passing therethrough when closed or when a catheter is inserted through the first valve 228 and/or the second valve 218. The first valve 228 and the second valve 218 can each be the same type of valve or they can each be a different type of valve. As will be appreciated, the first valve 228 and the second valve 218 can each be configured to withstand the pressure commonly present in vasculature such that little or no blood is permitted to escape through the hemostasis valve assembly 200.

The hemostasis valve assembly 200 can include a hollow tube 214 extending at least partially between the first valve 228 and the second valve 218. The hollow tube 214 can be sized to receive a mapping catheter, an ablation catheter, and/or other types of catheters. As will be described in greater detail herein, the hollow tube 214 can define apertures that can permit fluid and gas to pass therethrough. The hollow tube 214 can be configured to guide a catheter from the first valve 228 to the second valve 218 to ensure the catheter is directed through the second valve 218 into the sheath 106 and ultimately into the patient's vasculature. The hollow tube 214 and the expansion chamber body 202 can each have a length that is greater than a distal end of a catheter (e.g., the end effector) such that the distal end of the catheter can be entirely housed within the expansion chamber body 202 such that air bubbles released from the distal end of the catheter collect in the expansion chamber body 202.

The hemostasis valve assembly 200 can include an inlet chamber body 220, an expansion chamber body 202, and an end cap 208 that can together form a body and define an expansion chamber of the hemostasis valve assembly 200. The various components of the hemostasis valve assembly 200 just described can be attached together using adhesive, welding, press fit, or other methods of assembly known in the art.

FIG. 6A is a section view showing the components of the hemostasis valve assembly 200, in accordance with an example of the disclosed technology. As shown in FIG. 6A, the inlet chamber body 220 can include the lumen 112 which can extend therethrough, an inlet cap 222, an irrigation port adapter 226 configured to connect to the irrigation supply 120, and a first valve 228. The inlet chamber body 220 can define an inlet chamber 224 that can be configured to receive fluid from the irrigation supply and direct the fluid toward the expansion chamber body 202 and eventually through the second valve 218 and into the vasculature of the patient 23. As shown and described previously, the inlet chamber body 220 can be disposed outside of the handle 100, partially in the handle 100, or entirely in the handle 100 depending on the particular configuration.

As shown in FIG. 6A (see also FIGS. 8A and 8B), the expansion chamber body 202 can be attached to the inlet chamber body 220 and include a tubular portion 204 and a sloped portion 206. An end cap 208 can be attached to the distal end of the expansion chamber body 202 and include a sheath adapter 212 configured to receive and connect to the sheath 106. An O-ring or other seal 210 can be positioned between the end cap 208 and the expansion chamber body 202 to prevent fluid from escaping the expansion chamber body 202. In some examples, the seal 210 can include an adhesive positioned between the end cap 208 and the expansion chamber body 202.

The hemostasis valve assembly 200 can further include a tube adapter 216 that can be positioned between the hollow tube 214 and the end cap 208. The tube adapter 216 can be configured to align the hollow tube 214 in the expansion chamber body 202 with the second valve 218 and to secure the second valve 218 in place. For example, the tube adapter 216 can be attached to the end cap 208 and secure the second valve 218 between the tube adapter 216 and the end cap 208 to prevent the second valve 218 from becoming dislodged or otherwise moving out of position.

Figure 6B:
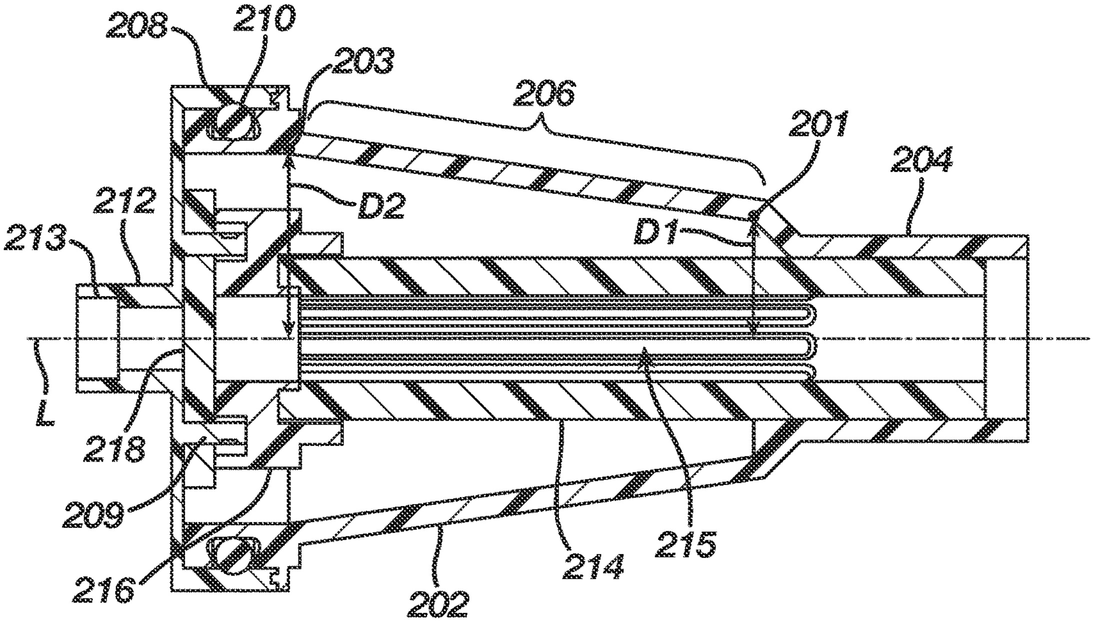
FIG. 6B is another section view showing the components of the hemostasis valve assembly, in accordance with an example of the disclosed technology.
Figure 7:
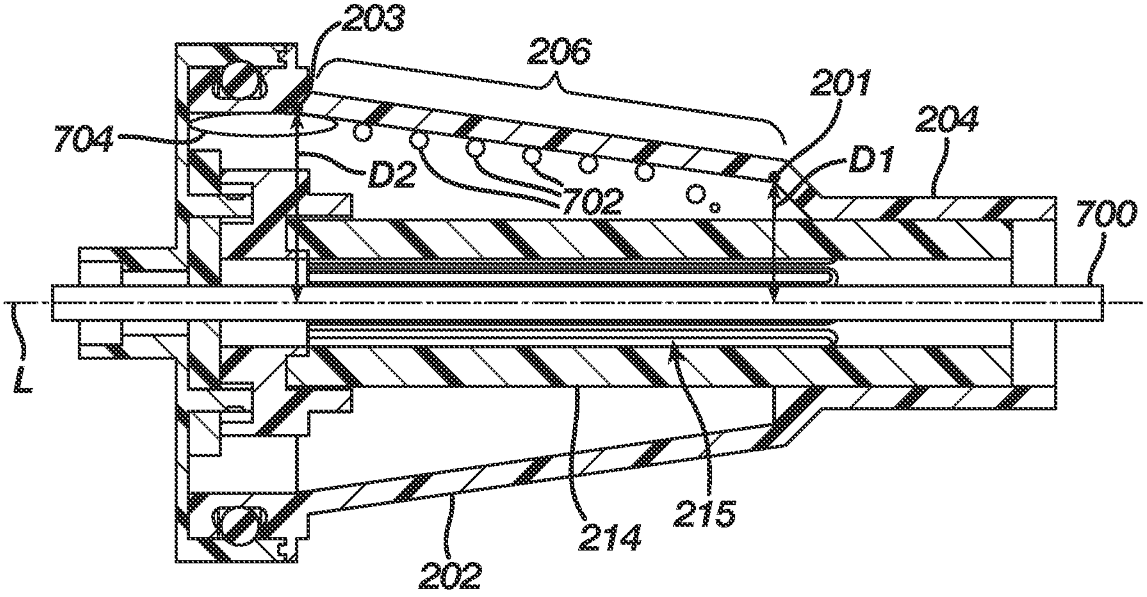
FIG. 7 is yet another section view showing the components of the hemostasis valve and air bubbles in the hemostasis valve assembly, in accordance with an example of the disclosed technology.

The tubular portion 204 of the expansion chamber body 202 can be configured to connect to the hollow tube 214 and the inlet chamber body 220. As shown in FIGS. 6B and 7, the sloped portion 206 can extend outward from the longitudinal axis L in the proximal direction to permit air or other gases to move upward toward the distal end of the expansion chamber body 202. As shown in FIG. 6B, a distance D1 between the longitudinal axis L and a first point 201 at the proximal end of the sloped portion 206 can be less than a distance D2 between the longitudinal axis and a second point 203 at the distal end of the sloped portion 206. As explained previously, as a catheter 700 (as shown in FIG. 7) is inserted through the first valve 228 and the second valve 218, air may inadvertently be introduced into the hemostasis valve assembly 200. Apertures 215 formed into the hollow tube 214 can permit gases to escape into the expansion chamber body 202. Because the sloped portion 206 slopes upward toward the distal end, gases (e.g., air) which have been introduced into the hemostasis valve assembly 200 can be guided along the sloped portion 206 to an accumulation region 704 wherein air bubbles 702 can collect. The accumulation region 704 can be positioned a sufficient distance away from the longitudinal axis and the second valve 218 to ensure gases that have entered the hemostasis valve assembly 200 are prevented from passing through the second valve 218. In some examples, the apertures 215 can include, or be replaced by, a permeable membrane configured to permit gases to pass there through but to prevent liquid (e.g., irrigation fluid or blood) from passing therethrough. In some examples, the permeable membrane can be or include a polydimethylsiloxane (PDMS) layer or polytetrafluoroethylene (PTFE) membranes or filters.

Figure 8A:
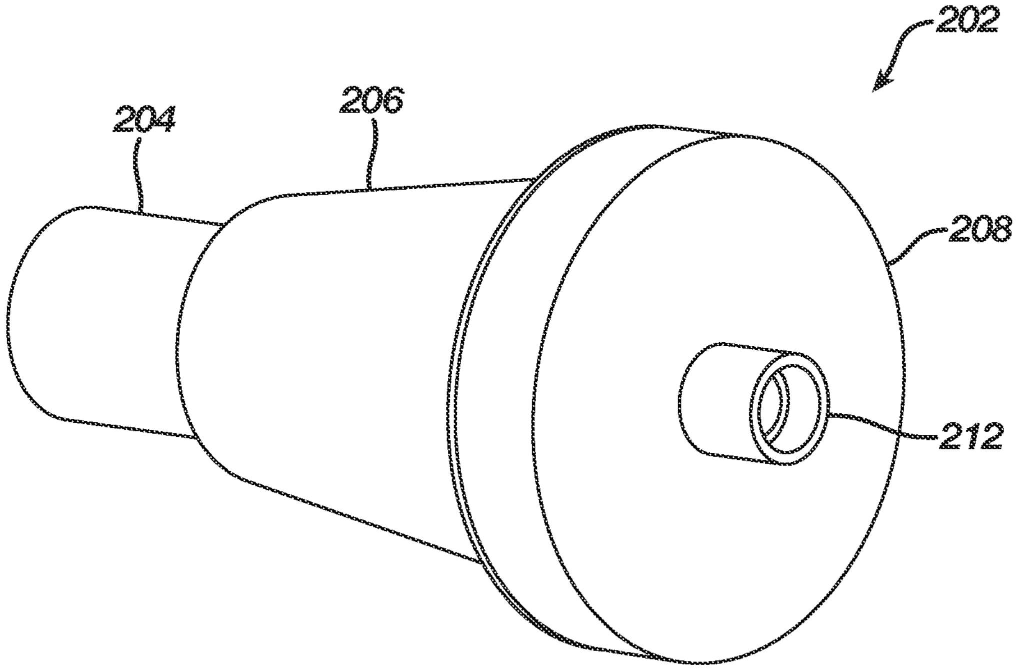
Figure 8B:
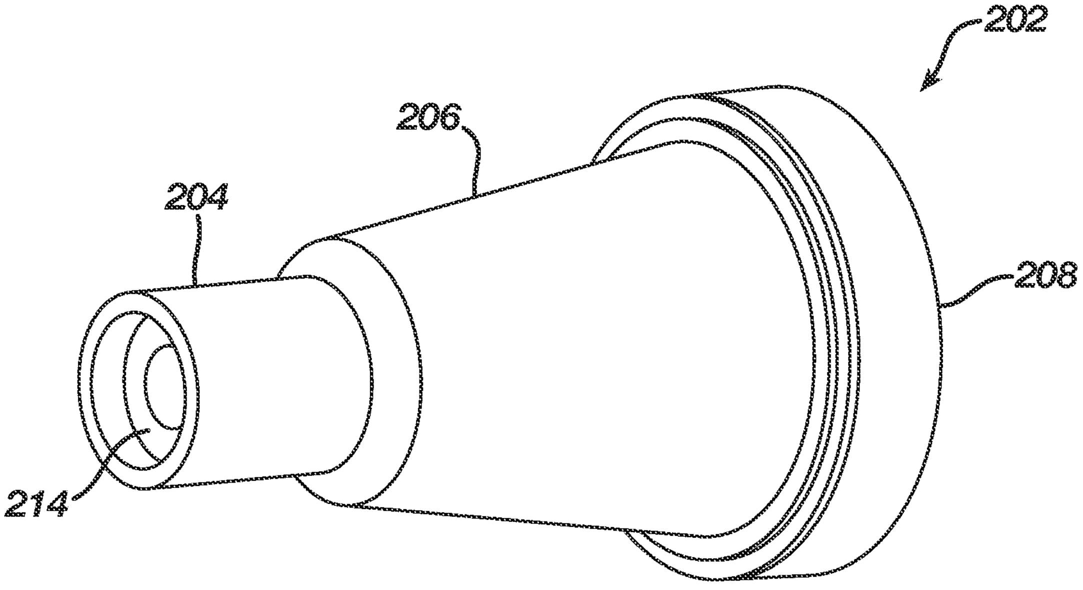
FIG. 8B is a rear perspective view of the hemostasis valve assembly, in accordance with an example of the disclosed technology.

As shown in FIGS. 8A and 8B, the expansion chamber body 202 can be rounded and form a funnel-like shape such that the sloped portion 206 can slope upwards no matter how the hemostasis valve assembly 200 is turned so long as the handle 100 is kept relatively level. That is to say that the expansion chamber body 202 can be approximately rotationally symmetric about the longitudinal axis L. In this way, the physician 24 can turn the handle 100 to manipulate the sheath 106 to ensure the distal end 110 is properly positioned with the hemostasis valve assembly 200 still being able to perform the function of directing gases away from the second valve 218.

Figure 9A:
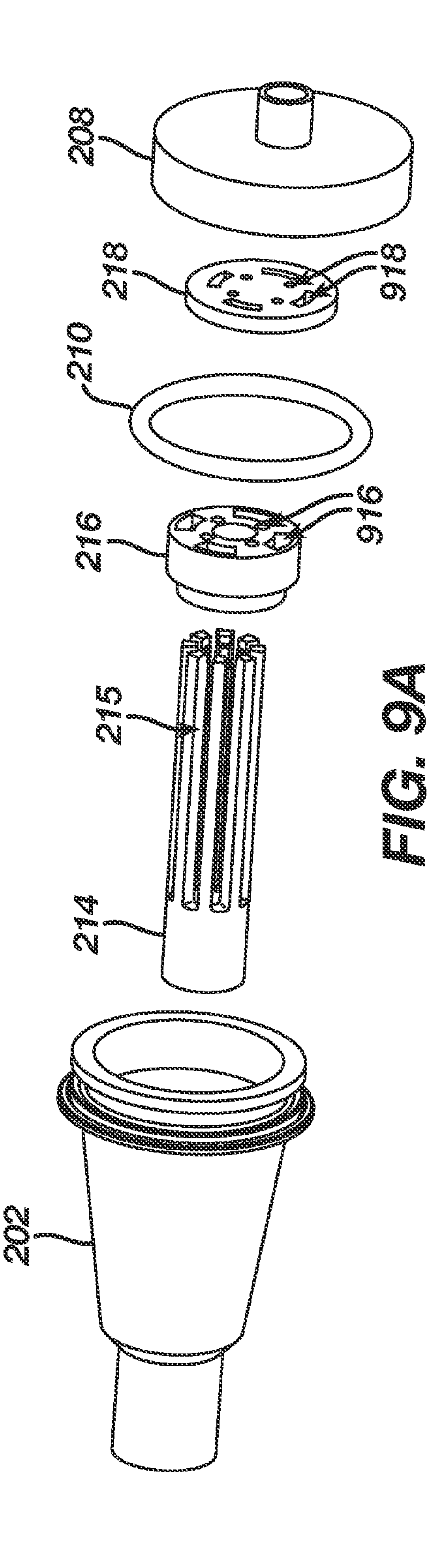
FIGS. 9A and 9B are perspective exploded views of the hemostasis valve assembly, in accordance with an example of the disclosed technology.
Figure 9B:
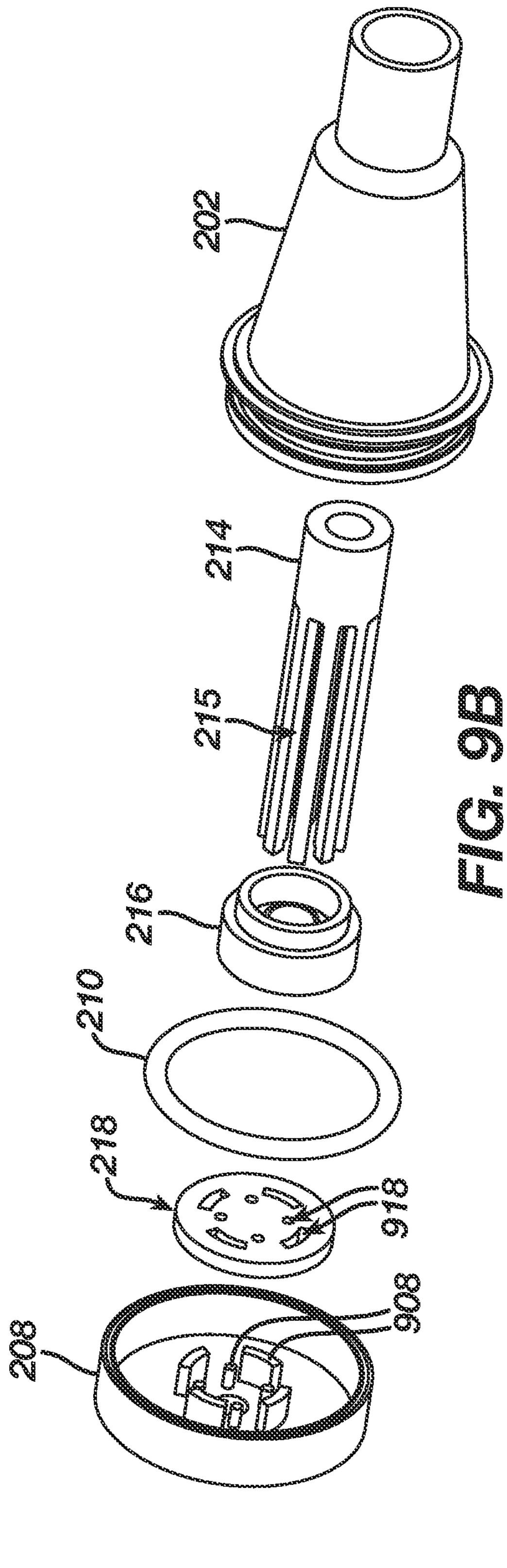
Figure 10A:
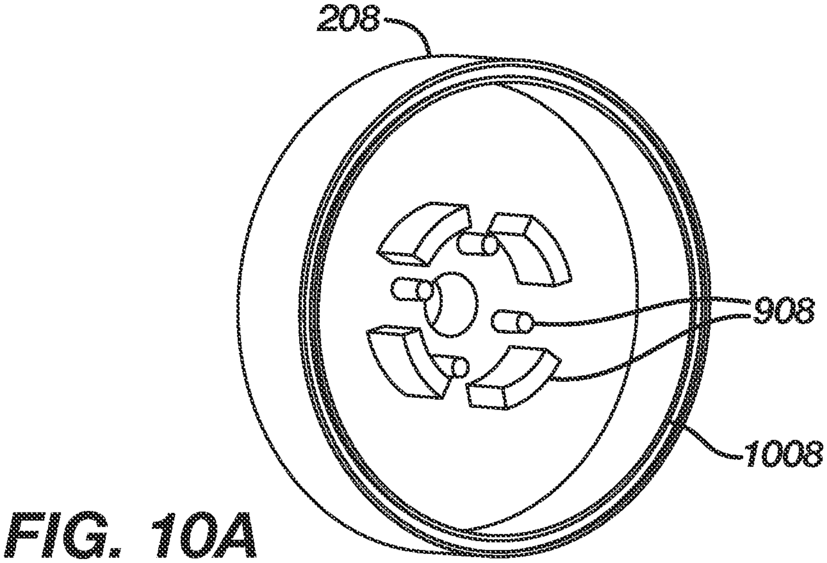
FIG. 10A is a perspective view of an end cap of the hemostasis valve assembly, in accordance with an example of the disclosed technology.

FIGS. 9A and 9B are perspective exploded views of the hemostasis valve assembly 200, in accordance with an example of the disclosed technology. As previously described, the hemostasis valve assembly 200 can include an expansion chamber body 202, a hollow tube 214, a tube adapter 216, a seal 210, a second valve 218, and an end cap 208. As shown in FIGS. 9A, the tube adapter 216 can include one or more apertures 916 configured to receive one or more protrusions 908 of the end cap. The one or more protrusions 908, shown in FIGS. 9B and 10A, can be configured to extend through one or more apertures 918 in the second valve 218 to help prevent the second valve 218 from becoming dislodged or otherwise moving out of position.

The tube adapter 216 can be further configured to receive at least a portion of the hollow tube 214 to help align a longitudinal axis of the hollow tube 214 with a longitudinal axis of the second valve 218 and the hemostasis valve assembly 200. The hollow tube 214 can define one or more apertures 215 extending therethrough in a direction perpendicular to the longitudinal axis L that can permit gas (e.g., air) to pass therethrough. As shown, the apertures 215 can include slots formed into the hollow tube 214 or the apertures 215 can have any other suitable shape, size, alignment, and/or configuration to permit gas to pass therethrough and accumulate in the accumulation region 704.

Figure 10B:
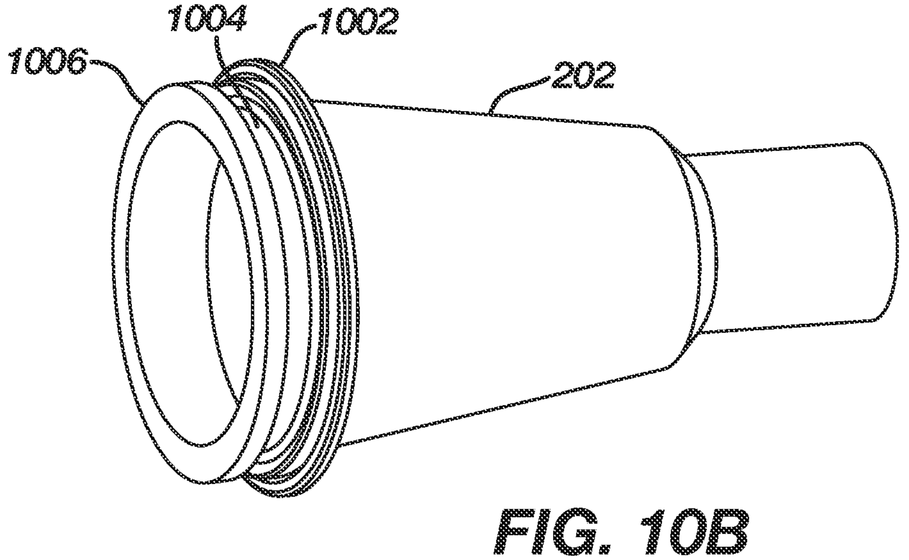
FIG. 10B is a perspective view of an elongate body of the hemostasis valve assembly, in accordance with an example of the disclosed technology.

As shown in FIG. 10B, the expansion chamber body 202 can include a first lip 1002, a second lip 1006, and a recess 1004 therebetween. The recess 1004 can be configured to receive the seal 210 and keep it in place. As will be appreciated, the recess 1004 can be sized to ensure the seal 210 extends outwardly a sufficient amount to form a liquid-tight seal between the expansion chamber body 202 and the end cap 208.

Figure 10C:
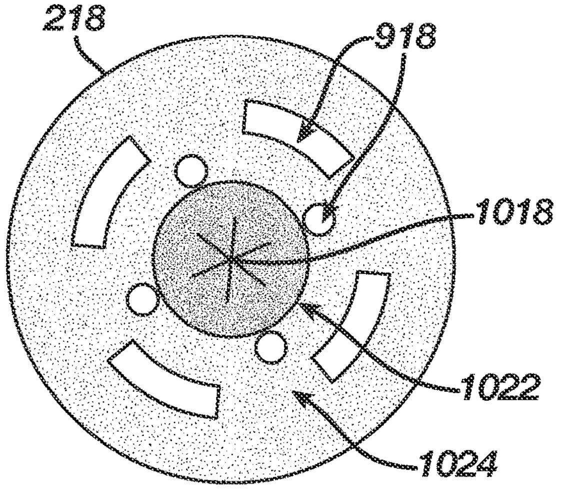
FIG. 10C is a front view of a valve of the hemostasis valve assembly, in accordance with an example of the disclosed technology.
Figure 10D:
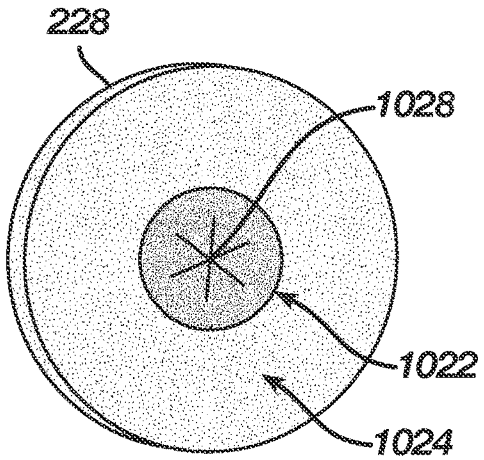
FIG. 10D is a perspective view of another valve of the hemostasis valve assembly, in accordance with an example of the disclosed technology.

As shown in FIGS. 10C and 10D, the first valve 228 can include a first opening 1028 and the second valve 218 can include a second opening 1018. The first opening 1028 and the second opening 1018 can be a slit configured to permit a catheter to be inserted therethrough while also forming a seal around the catheter, thereby preventing fluid from leaking through the first valve 228 and/or the second valve 218. The first valve 228 and/or the second valve 218 can include a first portion 1022 having a first durometer and a second portion 1024 having a second durometer. The first durometer can be less than the second durometer. In this way, the first valve 228 and/or the second valve 218 can have portions of the valve that will be more flexible or softer than others. For example, a first portion 1022 of the first valve 228 and/or the second valve 218 that is nearest the longitudinal axis L can have the first durometer to ensure sufficient flexibility while a second portion 1024 of the first valve 228 and/or the second valve 218 that is farthest from the longitudinal axis can have the second durometer to ensure the first valve 228 and/or the second valve 218 maintains a sufficient rigidity to withstand hemostatic pressure. Furthermore, the durometer of the first portion 1022 of the first valve 228 can be different than the durometer of the first portion 1022 of the second valve 218. Similarly, the durometer of the second portion 1024 of the first valve 228 can be different than the durometer of the second portion 1024 of the second valve 218.

Figure 10E:
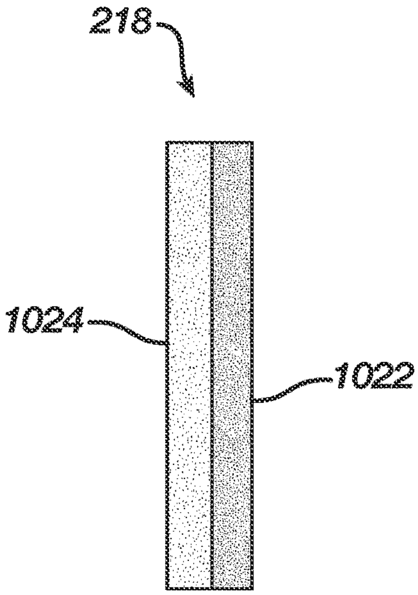
FIG. 10E is a side view of another valve of the hemostasis valve assembly, in accordance with an example of the disclosed technology.

As yet another example, as shown in FIG. 10E, the first portion 1022 and the second portion 1024 can be on a side of the first valve 228 and/or the second valve 218, rather than (or in addition to) being in a region of the first valve 228 and/or the second valve 218 as shown in FIGS. 10C and 10D. For example, a first side (e.g., the proximal side) of the first valve 228 and/or the second valve 218 can have a first portion 1022 having a first durometer and a second side (e.g., the distal side) can have a second portion 1024 having a second durometer. The first durometer can be less than the second durometer, or vice versa. For example, if the proximal side of the first valve 228 and/or the second valve 218 has a first portion 1022 comprising a lower durometer than the distal side having a second portion 1024, as a catheter is inserted through the first valve 228 and/or the second valve 218, the first portion 1022 which contacts the catheter shaft can help to form a liquid-tight seal. As another example, the overall durometer of the first valve 228 can be higher than an overall durometer of the second valve 218, and vice versa. For example, the first valve 228 can be made from material having a higher overall durometer than material used to make the second valve 218, even if the first valve 228 and/or the second valve 218 has a first portion 1022 and a second portion 1024. As will be appreciated, the chosen durometer of each first portion 1022 and each second portion 1024 of the valves 218, 228, as well as the overall durometer of the valves 218, 228 can be selected for the particular application and desired performance.

Figure 11:
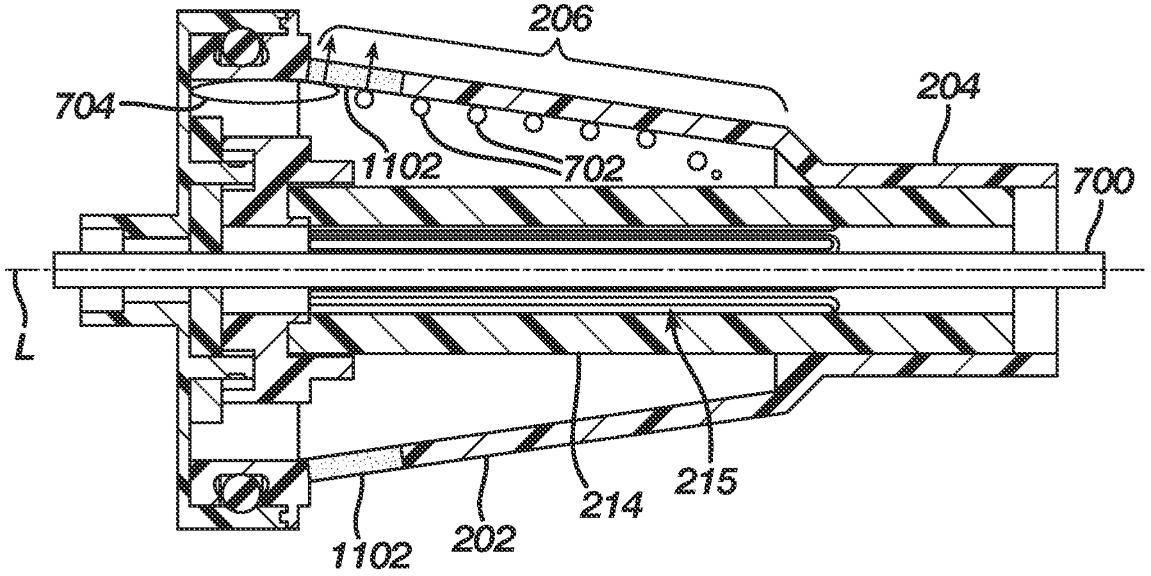
FIG. 11 is a section view of a hemostasis valve assembly, in accordance with another example of the disclosed technology.

Turning now to FIG. 11, the hemostasis valve assembly 200 can include a permeable membrane 1102 that can be configured to permit gases (e.g., air) to escape the expansion chamber body 202 while preventing liquid (e.g., saline and/or blood) from escaping. In this way, the gases which collect in the expansion chamber body 202 are prevented from building up to the point where gases could be forced through the second valve 218 by insertion of a catheter. Thus, as gases build up in the expansion chamber body 202, the gases will escape into the handle and then out into the atmosphere thereby preventing the gases from entering the vasculature. The permeable membrane 1102 can be any suitable permeable membrane 1102 capable of permitting gases to pass therethrough while still preventing the liquid from passing therethrough, even under pressure. For example, and not limitation, the permeable membrane 1102 can be or include a polydimethylsiloxane (PDMS) layer or polytetrafluoroethylene (PTFE) membranes or filters.

Figure 12:
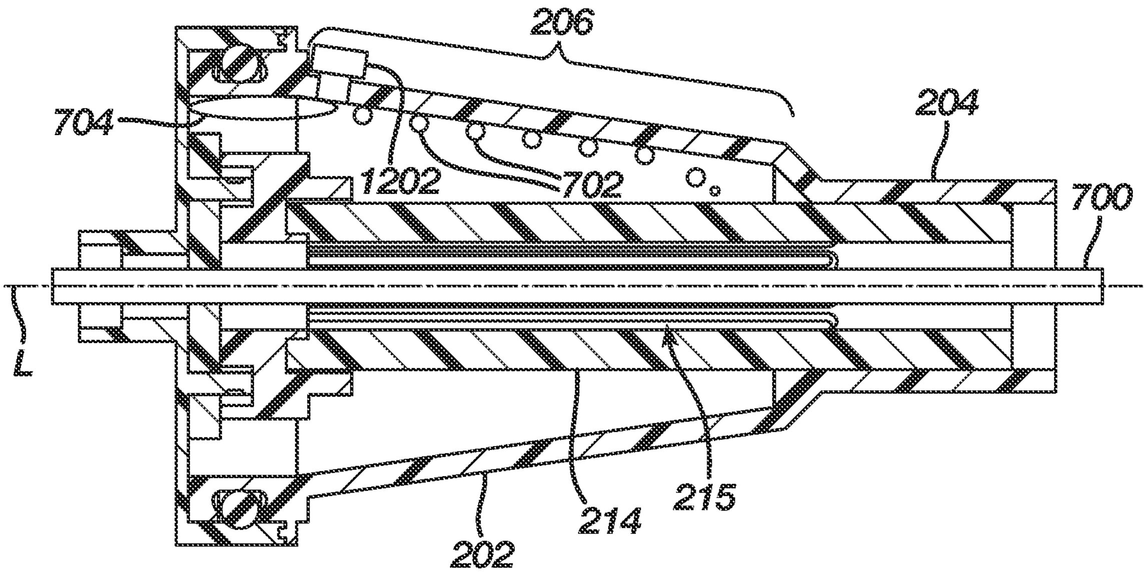
FIG. 12 is a section view of a hemostasis valve assembly, in accordance with yet another example of the disclosed technology.

FIG. 12 is a section view of another example of the hemostasis valve assembly 200, in accordance with an example of the disclosed technology. As shown in FIG. 12, the hemostasis valve assembly 200 can include a plug 1202 positioned near the accumulation region 704 (e.g., near the distal end of the expansion chamber body 202) and configured to be closed to prevent gases from passing therethrough or to be opened to allow gases to pass therethrough. The plug 1202, for example, can be opened by the physician 24 to permit any accumulated gases to escape the hemostasis valve assembly 200. In some examples, the plug 1202 can be a vent configured to permit gasses to pass therethrough but prevent liquid from passing therethrough. In some examples, at least a portion of the expansion chamber body 202 and at least a portion of the handle 100 can be made from transparent or semi-transparent material so that the physician 24 can see air bubbles as they accumulate. Thus, when the physician 24 determines that air has accumulated in the hemostasis valve assembly 200, the physician 24 can open the plug 1202 to permit the gases to escape therethrough. The plug 1202 can be any suitable type of plug, including but not limiting to, a threaded plug, a rubber plug, or various types of valves.

The disclosed technology described herein can be further understood according to the following clauses:

Clause 1: A hemostasis valve assembly comprising: an elongate body extending along a longitudinal axis and comprising a proximal end, a distal end, and a lumen extending therethrough; a first valve disposed near the proximal end of the elongate body, the first valve configured to allow a member to extend through the first valve; and a second valve disposed near the distal end of the elongate body spaced apart from the first valve, the second valve configured to allow the member to extend through the second valve, the elongate body defining a cavity comprising a sloped portion, the sloped portion including a first distance between an inner surface of the elongate body and the longitudinal axis near the distal end that is greater than a distance between the inner surface of the elongate body and the longitudinal axis near the proximal end such that a gas is directed along the sloped portion to accumulate at an accumulation region in the cavity near the distal end when a member extends through the first valve.

Clause 2: The hemostasis valve assembly according to clause 1 further comprising a hollow tube extending through the lumen from the first valve to the second valve.

Clause 3: The hemostasis valve assembly according to clause 2, the hollow tube defining one or more apertures extending therethrough perpendicular to the longitudinal axis.

Clause 4: The hemostasis valve assembly according to clause 3, the one or more apertures comprising slots formed into the hollow tube.

Clause 5: The hemostasis valve assembly according to any of clauses 2-4, the lumen being sized to receive a catheter device.

Clause 6: The hemostasis valve assembly according to any of the preceding clauses, at least one of the first valve and the second valve comprising a first portion including a first durometer and a second portion including a second durometer, the first durometer being less than the second durometer.

Clause 7: The hemostasis valve assembly according to clause 6, the first portion being a portion of the respective one of the first valve and second valve near the longitudinal axis and the second portion being a portion of the respective one of first valve and second valve near the elongate body.

Clause 8: The hemostasis valve assembly according to any of the preceding clauses, at least one of the first valve and the second valve comprising a slit near the longitudinal axis and a plurality of apertures formed therethrough a distance away from the longitudinal axis.

Clause 9: The hemostasis valve assembly according to clause 8, the elongate body further comprising a plurality of protrusions, the plurality of protrusions being configured to align with the plurality of apertures.

Clause 10: The hemostasis valve assembly according to any of the preceding clauses, the hemostasis valve assembly being configured to be disposed at least partially in a handle of a catheter device.

Clause 11: The hemostasis valve assembly according to any of the preceding clauses further comprising a plug disposed near the distal end of the elongate body, the plug configured to prevent fluid from exiting the elongate body when closed and to permit fluid to exit the elongate body when opened.

Clause 12: The hemostasis valve assembly according to any of the preceding clauses, the elongate body comprising a transparent material.

Clause 13: The hemostasis valve assembly according to any of the preceding clauses further comprising a permeable membrane disposed at the distal end of the elongate body, the permeable membrane configured to permit the gas to pass therethrough and to prevent a liquid from passing therethrough.

Clause 14: The hemostasis valve assembly according to clause 13, the permeable membrane comprising a polydimethylsiloxane (PDMS) layer.

Clause 15: The hemostasis valve assembly according to any of the preceding clauses the elongate body further comprising a proximal member and a distal member, the proximal member comprising the first valve and the distal member comprising the second valve.

Clause 16: The hemostasis valve assembly according to clause 15, the proximal member further comprising an irrigation port configured to receive an irrigation fluid from an irrigation fluid supply.

Clause 17: The hemostasis valve assembly according to clause 15 or clause 16, the distal member comprising an end cap and an expansion chamber, the expansion chamber comprising the sloped portion.

Clause 18: The hemostasis valve assembly according to clause 17, the distal member further comprising a sealing ring disposed between the end cap and the expansion chamber.

Clause 19: A handle for a catheter device, the handle comprising: a housing extending along a longitudinal axis, the housing configured for attachment to an insertion tube and comprising an inner chamber; a hemostasis valve assembly disposed at least partially in the inner chamber, the hemostasis valve assembly comprising: an elongate body extending along the longitudinal axis and comprising a proximal end, a distal end, and a lumen extending therethrough; a first valve disposed near the proximal end of the elongate body; and a second valve disposed near the distal end of the elongate body, the elongate body defining a cavity comprising a sloped portion, the sloped portion including a first distance between an inner surface of the elongate body and the longitudinal axis near the distal end that is greater than a distance between the inner surface of the elongate body and the longitudinal axis near the proximal end such that a gas is directed along the sloped portion to accumulate at an accumulation region in the cavity near the distal end.

Clause 20: The handle according to clause 19, the handle further comprising a proximal member and a distal member, the proximal member configured to support the first valve and the distal member comprising an end cap configured to support the second valve.

Clause 21: The handle according to clause 20, the proximal member extending at least partially beyond an outer boundary of the housing.

Clause 22: The handle according to clause 20 or 21, the proximal member further comprising an irrigation port configured to receive an irrigation fluid from an irrigation fluid supply.

Clause 23: The handle according to any of clauses 19-22, the end cap connected to the sloped portion to define an expansion chamber between the first valve and the second valve.

Clause 24: The handle according to any of clauses 19-22 further comprising a hollow tube extending through the lumen from the first valve to the second valve.

Clause 25: The handle according to clause 24, the hollow tube being disposed in the expansion chamber.

Clause 26: The handle according to clause 24, the hollow tube defining one or more apertures extending therethrough perpendicular to the longitudinal axis.

Clause 27: The handle according to clause 26, the one or more apertures comprising slots formed into the hollow tube.

Clause 28: The handle according to any of clauses 19-27, the lumen being sized to receive a catheter device.

Clause 29: The handle according to any of clauses 19-28, the distal member further comprising a sealing ring disposed between the end cap and the expansion chamber.

Clause 30: The handle according to any of clauses 19-29, at least one of the first valve and the second valve comprising a first portion including a first durometer and a second portion including a second durometer, the first durometer being less than the second durometer.

Clause 31: The handle according to clause 30, the first portion being a portion of the respective one of the first valve and second valve near the longitudinal axis and the second portion being a portion of the respective one of the first valve and second valve near the elongate body.

Clause 32: The handle according to any of clauses 19-31, at least one of the first valve and the second valve comprising a slit near the longitudinal axis and a plurality of apertures formed therethrough a distance away from the longitudinal axis.

Clause 33: The handle according to clause 32, the elongate body further comprising a plurality of protrusions, the plurality of protrusions being configured to align with the plurality of apertures.

Clause 34: The handle according to any of clauses 19-33 further comprising a plug disposed near the distal end of the elongate body, the plug configured to prevent fluid from exiting the elongate body when closed and to permit fluid to exit the elongate body when opened.

Clause 35: The handle according to any of clauses 19-34, the elongate body comprising a transparent material.

Clause 36: The handle according to any of clauses 19-35 further comprising a permeable membrane disposed at the distal end of the body, the permeable membrane configured to permit a gas to pass therethrough and to prevent a liquid from passing therethrough.

Clause 37: The handle according to clause 36, the permeable membrane comprising a polydimethylsiloxane (PDMS) layer.

The embodiments described above are cited by way of example, and the present invention is not limited by what has been particularly shown and described hereinabove. Rather, the scope of the invention includes both combinations and sub combinations of the various features described hereinabove, as well as variations and modifications thereof which would occur to persons skilled in the art upon reading the foregoing description and which are not disclosed in the prior art.

What is claimed is:

1. A hemostasis valve assembly comprising:

an elongate body extending along a longitudinal axis and comprising a proximal end, a distal end, and a lumen extending therethrough;

a first valve disposed near the proximal end of the elongate body, the first valve configured to allow a member to extend through the first valve;

a second valve disposed near the distal end of the elongate body spaced apart from the first valve, the second valve configured to allow the member to extend through the second valve; and a permeable membrane disposed at the distal end of the elongate body, the permeable membrane configured to permit a gas to pass therethrough and to prevent a liquid from passing therethrough, the elongate body defining a cavity comprising a sloped portion, the sloped portion including a first distance between an inner surface of the elongate body and the longitudinal axis near the distal end that is greater than a distance between the inner surface of the elongate body and the longitudinal axis near the proximal end such that the gas is directed along the sloped portion to accumulate at an accumulation region in the cavity near the distal end when a member extends through the first valve.

2. The hemostasis valve assembly according to claim 1, further comprising a hollow tube extending through the lumen from the first valve to the second valve.

3. The hemostasis valve assembly according to claim 2, the hollow tube defining one or more apertures extending therethrough perpendicular to the longitudinal axis.

4. The hemostasis valve assembly according to claim 1, at least one of the first valve and the second valve comprising a first portion including a first durometer and a second portion including a second durometer, the first durometer being less than the second durometer.

5. The hemostasis valve assembly according to claim 4, the first portion being a portion of the respective one of the first valve and second valve near the longitudinal axis and the second portion being a portion of the respective one of first valve and second valve near the elongate body.

6. The hemostasis valve assembly according to claim 1, at least one of the first valve and the second valve comprising a slit near the longitudinal axis and a plurality of apertures formed therethrough a distance away from the longitudinal axis.

7. The hemostasis valve assembly according to claim 6, the elongate body further comprising a plurality of protrusions, the plurality of protrusions being configured to align with the plurality of apertures.

8. The hemostasis valve assembly according to claim 1, the hemostasis valve assembly being configured to be disposed at least partially in a handle of a catheter device.

9. The hemostasis valve assembly according to claim 1, further comprising a plug disposed near the distal end of the elongate body, the plug configured to prevent fluid from exiting the elongate body when closed and to permit fluid to exit the elongate body when opened.

10. The hemostasis valve assembly according to claim 1, the elongate body comprising a transparent material.

11. The hemostasis valve assembly according to claim 1, the permeable membrane comprising a polydimethylsiloxane (PDMS) layer.

12. The hemostasis valve assembly according to claim 1, further comprising an irrigation port configured to receive an irrigation fluid from an irrigation fluid supply.

13. A handle for a catheter device, the handle comprising:

a housing extending along a longitudinal axis, the housing configured for attachment to an insertion tube and comprising an inner chamber;

a hemostasis valve assembly disposed at least partially in the inner chamber, the hemostasis valve assembly comprising:

an elongate body extending along the longitudinal axis and comprising a proximal end, a distal end, and a lumen extending therethrough;

a first valve disposed near the proximal end of the elongate body;

a second valve disposed near the distal end of the elongate body; and a proximal member and a distal member, the proximal member configured to support the first valve and the distal member comprising an end cap configured to support the second valve, the elongate body defining a cavity comprising a sloped portion, the sloped portion including a first distance between an inner surface of the elongate body and the longitudinal axis near the distal end that is greater than a distance between the inner surface of the elongate body and the longitudinal axis near the proximal end such that a gas is directed along the sloped portion to accumulate at an accumulation region in the cavity near the distal end.

14. The handle according to claim 13, the proximal member extending at least partially beyond an outer boundary of the housing.

15. The handle according to claim 14, the proximal member further comprising an irrigation port configured to receive an irrigation fluid from an irrigation fluid supply.

16. The handle according to claim 15, the end cap connected to the sloped portion to define an expansion chamber between the first valve and the second valve.

17. The handle according to claim 13, further comprising a hollow tube extending through the lumen from the first valve to the second valve.

18. The handle according to claim 17, the hollow tube defining one or more apertures extending therethrough perpendicular to the longitudinal axis.

* * * * *